(12) United States Patent
Hickok

(10) Patent No.: US 6,817,862 B2
(45) Date of Patent: Nov. 16, 2004

(54) ULTRASONIC DENTAL TOOL HAVING QUICK CHANGE CONNECTOR AND METHOD OF MAKING SAME

(75) Inventor: Teresa R. Hickok, Bonita, CA (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 10/649,455

(22) Filed: Aug. 26, 2003

(65) Prior Publication Data

US 2004/0038175 A1 Feb. 26, 2004

Related U.S. Application Data

(62) Division of application No. 10/067,155, filed on Feb. 4, 2002, which is a continuation of application No. 09/326,046, filed on Jun. 4, 1999, now abandoned.

(51) Int. Cl.[7] .................................................. A61C 1/07
(52) U.S. Cl. ...................................... 433/119; 433/127
(58) Field of Search ........................... 433/86, 119, 126, 433/127, 128, 129; 279/37; 403/184, 289, 290, 409.1

(56) References Cited

U.S. PATENT DOCUMENTS

| | | | |
|---|---|---|---|
| 2,921,372 A | 1/1960 | Bodine, Jr. ........................ 32/27 |
| 3,076,904 A | 2/1963 | Kleesattel et al. ............. 310/26 |
| 3,124,878 A | 3/1964 | Bodine, Jr. ........................ 32/36 |
| 3,368,280 A | 2/1968 | Friedman et al. ................ 32/58 |
| 3,488,851 A | 1/1970 | Haydu ............................. 32/58 |
| 3,518,766 A | * 7/1970 | Burt .............................. 433/86 |
| 3,589,012 A | 6/1971 | Richman ......................... 32/58 |
| 3,593,425 A | 7/1971 | Robinson ........................ 32/58 |
| 3,645,255 A | 2/1972 | Robinson ....................... 128/24 |
| 3,654,502 A | 4/1972 | Carmona et al. ............. 310/26 |
| 3,703,037 A | 11/1972 | Robinson ........................ 32/58 |
| 3,919,524 A | * 11/1975 | Fortune ......................... 219/238 |
| 3,924,335 A | 12/1975 | Balamuth et al. .............. 32/58 |
| 3,930,173 A | 12/1975 | Banko .......................... 310/26 |
| 3,956,826 A | 5/1976 | Perdreaux ...................... 32/58 |
| 4,038,571 A | 7/1977 | Hellenkamp ................ 310/8.2 |
| 4,048,723 A | 9/1977 | Thorup .......................... 32/40 |
| 4,110,908 A | 9/1978 | Cranston ........................ 32/50 |
| 4,168,447 A | 9/1979 | Bussiere et al. ............. 310/316 |
| 4,169,984 A | 10/1979 | Parisi ........................... 310/323 |
| 4,193,196 A | 3/1980 | Kuris et al. .................... 433/82 |
| 4,260,380 A | 4/1981 | Nash ........................... 433/119 |
| 4,276,880 A | 7/1981 | Malmin ....................... 128/221 |
| 4,283,175 A | 8/1981 | Nash ........................... 433/119 |
| 4,315,742 A | 2/1982 | Nash et al. .................... 433/86 |
| 4,330,278 A | 5/1982 | Martin .......................... 433/81 |
| 4,332,558 A | 6/1982 | Lustig ........................... 433/86 |
| 4,370,131 A | 1/1983 | Banko ........................... 433/86 |

(List continued on next page.)

FOREIGN PATENT DOCUMENTS

| | | |
|---|---|---|
| DE | 26 37 176 | 8/1976 |
| DE | 30 32 022 | 3/1982 |
| DE | 33 28 605 | 8/1983 |
| EP | 0 261 272 | 9/1986 |
| EP | 0898941 | 3/1999 |
| FR | 2143251 | 6/1972 |
| FR | 2550439 | 6/1984 |
| FR | 2566262 | 6/1984 |
| JP | 1-212547 | 11/1987 |

*Primary Examiner*—Todd E. Manahan
(74) *Attorney, Agent, or Firm*—McNees Wallace & Nurick LLC; Carmen Santa Maria; Jonathan P. Miller

(57) ABSTRACT

A dental tool for use with an ultrasonic transducer, the tool comprises a substantially elongate tool defined by a shaft having a proximal end with a coupling attachment at the proximal end for attachment to an ultrasonic transducer, and a distal end having a tip configured for performing a dental procedure, and a fluid passage extending from the proximal end to a port configured and positioned to direct fluid onto the tip.

7 Claims, 4 Drawing Sheets

U.S. PATENT DOCUMENTS

| | | | |
|---|---|---|---|
| 4,427,384 A | 1/1984 | Sertich | 433/120 |
| 4,453,919 A | 6/1984 | Takeshita | 433/120 |
| 4,578,033 A | 3/1986 | Mossle et al. | 433/20 |
| 4,589,847 A | 5/1986 | Loge et al. | 433/126 |
| 4,634,376 A | 1/1987 | Mossle et al. | 433/29 |
| 4,820,152 A | 4/1989 | Warrin et al. | 433/86 |
| 5,082,443 A | 1/1992 | Lohn | 433/80 |
| 5,125,837 A | 6/1992 | Warrin et al. | 433/98 |
| 5,190,456 A | 3/1993 | Hasegawa | 433/120 |
| 5,531,597 A | 7/1996 | Foulkes et al. | 433/119 |
| 5,567,153 A | 10/1996 | Foulkes et al. | 433/119 |
| 5,725,370 A * | 3/1998 | Himeno et al. | 433/86 X |
| 5,733,119 A | 3/1998 | Carr | 433/119 |
| 5,749,727 A | 5/1998 | Dao et al. | 433/119 |
| 6,062,858 A | 5/2000 | Hugo | 433/119 |

* cited by examiner

ULTRASONIC DENTAL TOOL HAVING QUICK CHANGE CONNECTOR AND METHOD OF MAKING SAME

This application is a divisional application of Application No. 10/067,155 filed Feb. 4, 2002, which is a continuation of Application No. 09/326,046 filed Jun. 4, 1999 now abandoned, claiming priority to these applications.

FIELD OF THE INVENTION

This invention relates generally to ultrasonic dental tools and pertains more particularly to special micro endodontic ultrasonic surgical and dental tools having a water port.

BACKGROUND

In the last four to five years microdentistry began to develop. Microdentistry is the performing of dental surgery and procedures with very small tools under a microscope. As an example, in the preparation of root canals, it has been found that the tool must be very small in order to work in the small canal areas. Such small tools must also be very strong and tough and able to withstand and/or easily dissipate and/or resist heat.

In recent years ultrasonic tools have been developed which many dental surgeons have begun to use for many operations on teeth, bones, and soft tissue including dislodging and removal of dental material. These ultrasonic tools have been found to be particularly useful for microdentistry and particularly for use in root canals. Tools for this purpose must be small, hard, durable and heat resistant in order to satisfactorily perform their function. They must also be flushed with a fluid such as water to dissipate heat and flush away debris.

Recent years have seen greater use of ultrasonically powered instruments for the preparation of root canals. Examples of ultrasonically powered instruments of this type for the preparation of root canals are disclosed in U.S. Pat. No. 4,019,254, issued Apr. 26, 1977 to Malmin, U.S. Pat. No. 5,094,617 issued Mar. 10, 1992 to Carr and PCT Publication WO 86/05967. With the exception of the first mentioned patent, all tools are formed with a shaft tapered to a point. More recent examples of improved tools are disclosed in the applicant's recently issued U.S. Pat. No. 5,836,765, issued Nov. 17, 1998, and U.S. Pat. No. 5,868,570 issued Nov. 12, 1998 to Hickok.

Most dental tools and work areas are cooled with a continuous stream of water during use. Cooling in this manner is not always possible, particularly when working in certain small confined areas such as root canals, and in most instances this form of cooling is inconvenient.

In the past, fluid such as water has been supplied to the cutting tool by means of either a separate water supply such as a wand or the like, or a supply through or from the adjacent power unit. The tools normally used with ultrasonic generators are typically very small and must be hard and durable to withstand the high energy delivered by the ultrasonic generator. Due to the size and the materials from which the tools are made, it has not been possible to provide a through the tool fluid supply to the tool and word area.

One example of an earlier dental tool having a fluid supply to the tip is U.S. Pat. No. 3,924,335 dated Dec. 20, 1975. The patent discloses a metal or plastic transmission member which has a water feed to be used as a dental prophylaxis unit for removing deposits from tooth and gingival surfaces. However, this tool is not suitable for microdentistry.

U.S. Pat. No. 4,193,196 discloses a fluid supply unit for dental instruments wherein an instrument is shown with flow through tip. This tool is not disclosed as suitable for microdentistry.

U.S. Pat. No. 5,733,119 discloses a dental tool having fluid supply port in the hub of the tool. These tools of the prior art cannot be made sufficiently small to function as a microdentistry tool and provide the fluid port in the shaft of the tool at the working tip.

Therefore, there is a need for an improved ultrasonic dental tool formed of a suitable strong, flexible and durable heat resistant material with suitable fluid port for microdentistry.

Another drawback to these tools is that they are attached and detached from the hand piece of the ultrasonic generator by means of a threaded connection requiring a wrench or other special tool. This is particularly inconvenient because several different shape tools are frequently required during any particular operation.

Therefore, there is also a need for an improved ultrasonic dental tool having a quick attach connector for microdentistry.

SUMMARY OF THE INVENTION

A primary objective of this invention is to provide an improved ultrasonic dental tool having a tip that is formed of durable high strength heat resistant material and has a port for delivery of fluid to the tip.

Another objective is to provide a tool of a suitable material that can be made small enough for MICROENDODONTICS that has provision for delivery of a fluid to the tip.

In accordance with a primary aspect of the present invention a dental tool for use with an ultrasonic transducer comprises a substantially elongate tool defined by a shaft having a proximal end with means for attachment to an ultrasonic transducer, and a distal end having a tip configured for performing a dental procedure, an fluid passage extending from the proximal end to a port positioned and configured to direct fluid on the tip.

BRIEF DESCRIPTION OF DRAWINGS

The objects, advantages and features of this invention will be more readily appreciated from the following detailed description, when read in conjunction with the accompanying drawing, in which.

DETAILED DESCRIPTION OF PREFERRED EMBODIMENTS

Figure 1:
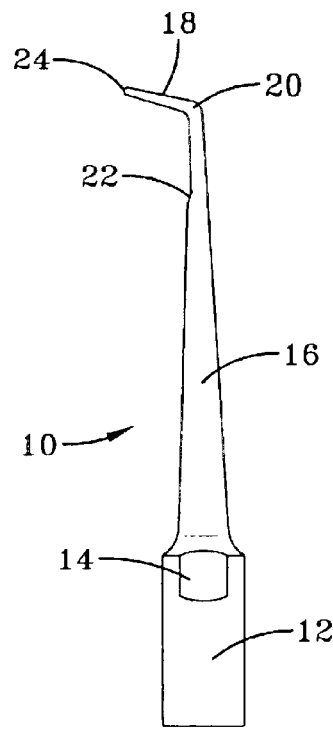
FIG. 1 is a side elevation view of an ultrasonic dental tool constructed in accordance with a preferred embodiment of the invention.

The present invention is described with reference to preferred embodiments of the invention as illustrated in the drawings. While this invention is described in terms of the best mode for achieving this invention's objectives, it will be appreciated by those skilled in the art that variations may be made in view of these teachings without deviating from the spirit or scope of the invention.

Figure 2:
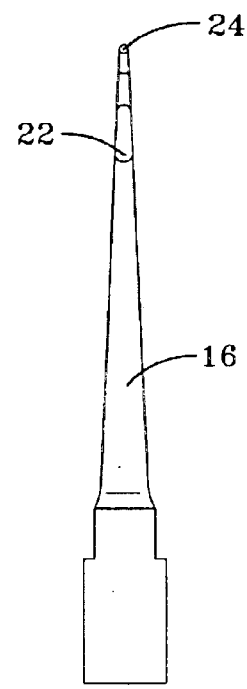
FIG. 2 is a front elevation view of the tool of FIG. 1.

Referring to FIGS. 1 and 2 of the drawings there is illustrated an exemplary embodiment of a tool for dental surgical operations, in accordance with the present invention, designated generally by the numeral 10. The tool 10 is devised to get water or fluid to the working edge of the surgical tip of endodontic work tool. The tips are constructed with a tip on the order of one sixty-fourths inch in diameter at the point versus about one sixteenth of an inch for prior art tools. For this reason the tools are constructed of a medical grade titanium alloy or a stainless steel alloy.

The inventor has found that titanium, which is not normally considered a tool material, performs well as a dental tip, particularly for use ultrasonic generators. Suitable titanium materials are covered in more detail in the inventors U.S. Pat. No. 5,836,765 granted Nov. 17, 1998, which is incorporated herein by reference as though fully set forth. The tool may also be made of either 17-4 PH or 13-8 MO stainless steel. The tool as shown may be detachably connected to an ultrasonic vibrator or transducer (not shown) of generally well-known conventional construction for carrying out microdental surgical procedures.

The tool, as illustrated, comprises an elongated shank having connecting means 12 at a proximal end. The connection means is shown in the form of a threaded socket for threadably mounting on the end of a shaft and having a flat 14 on each side for engagement by a wrench or the like for threadably tightening and loosening the tool.

The tool is formed with an elongated tapered shank or shaft 16 which has a distal end portion 18 which is curved away from the shank to form what is commonly called a tip. The tip as used herein means that portion of the tool between the curve or bend at 20 and the point 24. This tip portion is curved or bent at 20 in a direction away from the axis of the shank at an angle of preferably about 75–85°, extending away from the proximal end. This tip portion is the cutting or working portion of the tool. The tool is designed primarily to perform root canals which are preferably performed from the root end of the tooth. These tools as provided herein enable the performance or an operation wherein the tooth is removed, the root canal work performed and the tooth reinstalled. This procedure must be carried out in less than ten minutes in order for the tooth to survive.

The tool is formed with a fluid outlet port 22 which communicates fluid via an elongated axial passage from the proximal or connecting end of the tool. The outlet port 22 is positioned and configured to direct fluid such as water onto the tip 18 and into the working area to flush debris therefrom. The port may be positioned closer or further away from the bend 20 to achieve the desired placement of the fluid. As can be seen the tip extends in front of the outlet port.

The shank portion 16 extends outward from the connecting collar 12 and is of a generally uniform taper in a manner, as illustrated. The shank portion or section 16 of the shaft tapers gradually down to a distal or working end portion 18, or tip, which may have a sharpened point or other form. This portion 22 is the primary working portion and may have a length of from about one eight (⅛) to about three sixteenth (3/16) inch or three to about five mm. When constructed of stainless steel this portion typically has a diameter of about 0.015 to about 0.0250 inches or about 0.4 to 0.6 mm when made of stainless steel called for herein. The length can also be extended up to about 25 mm and the diameter reduced about 0.015 inches or 0.4 to 0.6 mm when constructed of titanium.

Figure 3:
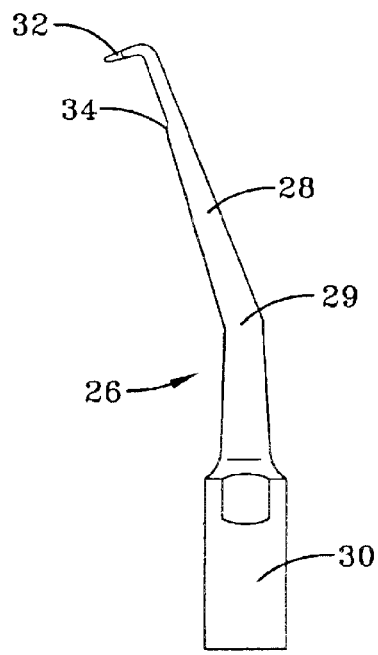
FIG. 3 is a side elevation view of an alternate embodiment of an ultrasonic dental tool.

Referring to FIG. 3, an alternate embodiment of an ultrasonic tool is illustrated, designated generally at 26 and comprising an elongated shank 28, having connecting means or hub 30 at a proximal end with the shank tapering down at a reduced diameter from the connecting hub with a substantially uniform taper along a shaft to a tip 32. The shaft is formed with a bend at 29 between the hub 30 and the tip 32. A fluid outlet port 34 communicates fluid as in the prior embodiment via an elongated passage from the proximal or connecting end of the tool to the tip. The outlet port 34 is positioned and configured to direct fluid such as water onto the tip 32 and into the work area. The port, as illustrated, is shown positioned closer to the bend than in the prior embodiment for desired placement of the fluid. This tool may be used to perform any number of dental procedures and may be hardened or coated with suitable means for roughening or the like to create an abrasive surface, if desired.

Figure 4:
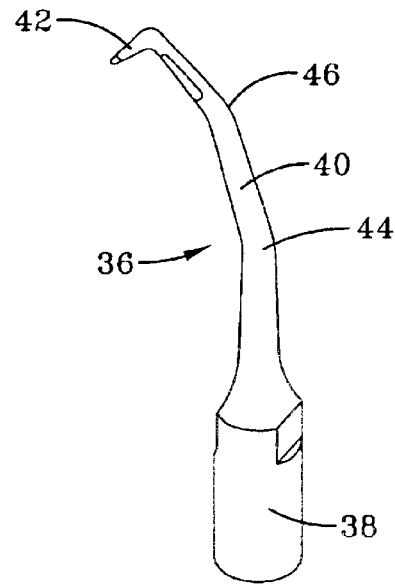
FIG. 4 is a front elevation view of an another embodiment of an ultrasonic dental tool.

Referring to FIG. 4, another embodiment having a complex curved configuration is illustrated and designated generally by the numeral 36 having a connecting hub 38 with an elongated tapered shaft 40 down to a pointed tip 42 extending upward at an angle to close to 90° from the axis of the shaft 40. The angle of the tip may vary from less than 90° to greater than 90°, such as from about 75 to about 90 degrees, as desired. The shaft 40 is provided with a complex set of bends or curvatures at 44 and 46 between the hub and the tip. The complex curved configuration enables the tool to reach difficult areas within the oral cavity. The shaft can have any number of bends and configurations such as disclosed in the inventors prior U.S. Pat. No. 5,868,570 incorporated herein by reference. This tip may also be suitably roughened and coated as necessary to perform the necessary function.

Figure 5:
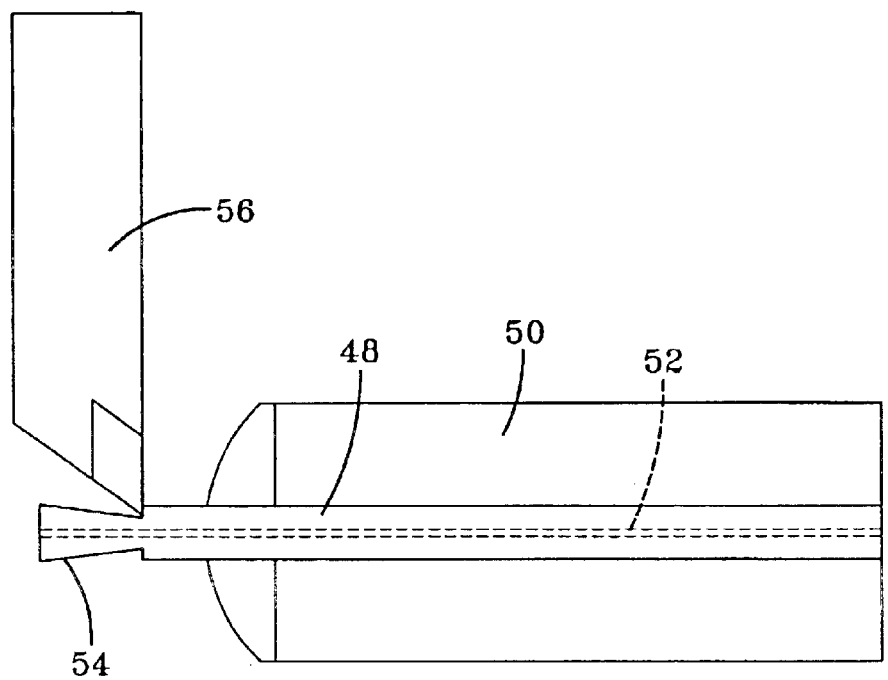
FIG. 5 is a side elevation view illustrating an early step in the machining process of making tools in accordance with the invention.

The applicant has devised a novel method of making the tools in accordance with the present invention. Referring to FIG. 5, an early step in the process is illustrated wherein a suitable bar stock 48 of suitable material from which to make the tool is selected and mounted in a chuck in a lathe extending through a guide bushing 50. The bar stock is preferably cylindrical with a central bore 52 extending the length thereof. The bar stock which has a diameter of about 0.187 inch or 3.5 mm with a central bore of about 0.020 inch or 0.5 mm is placed in the chuck of the lathe extending through the guide bushing with a length of the stock extending beyond the end of the guide bushing. A small tapered portion 54 is turned by a cutting tool 56 on a forward end of the bar stock to establish a bend point and the location of the fluid port.

Figure 6:
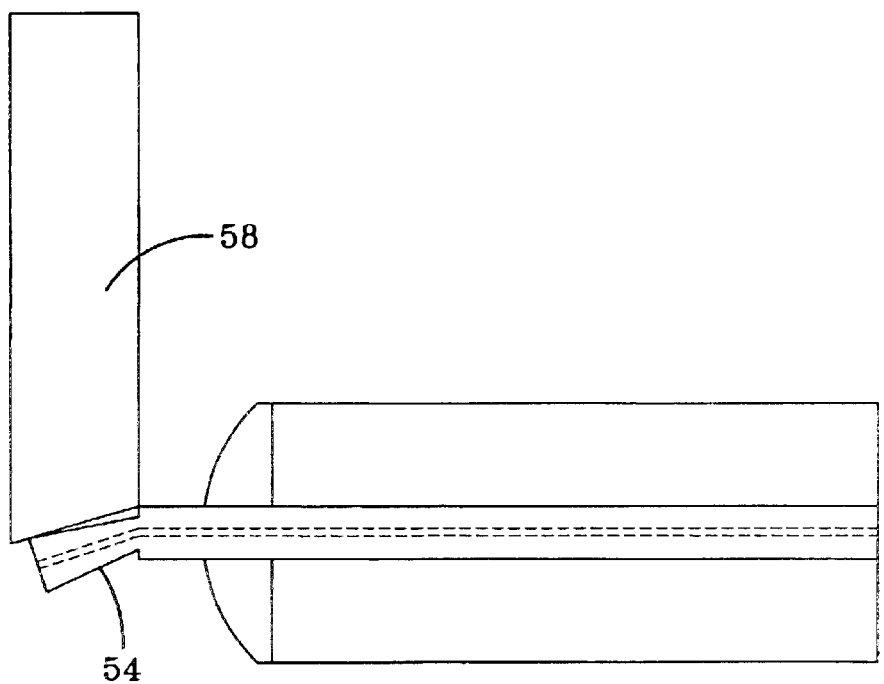
FIG. 6 is a view like FIG. 5 illustrating an early step in the machining process of making tools in accordance with the invention.

Referring to FIG. 6, the turned end portion 54 is bent by a tool 58 out of alignment with the axis of the elongated stock. The tapered portion is bent off-center by the bending tool to allow the central hole or bore to run out the side of the bar when the bar is further turned to form the shaft of the tool.

Figure 7:
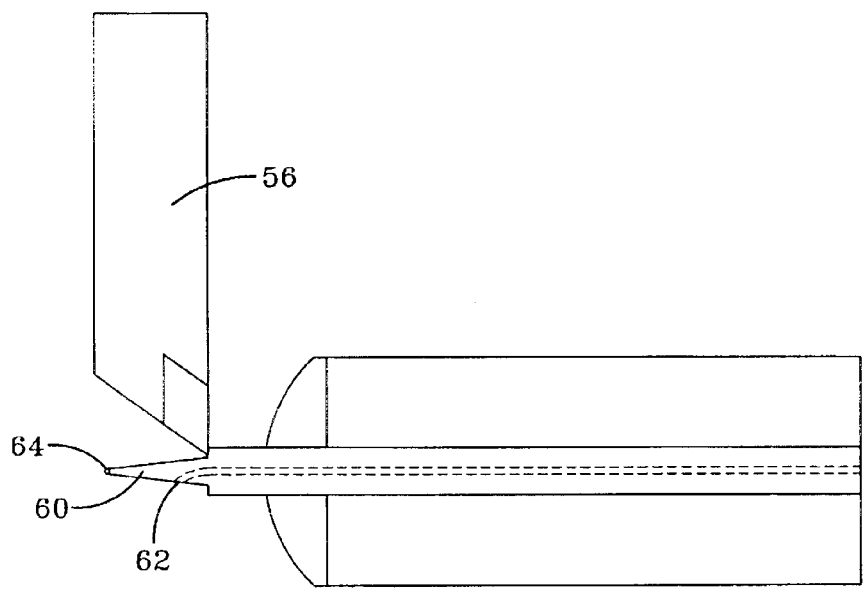
FIG. 7 is a view like FIG. 6 illustrating a further step in the machining process of making tools in accordance with the invention.
Figure 8:
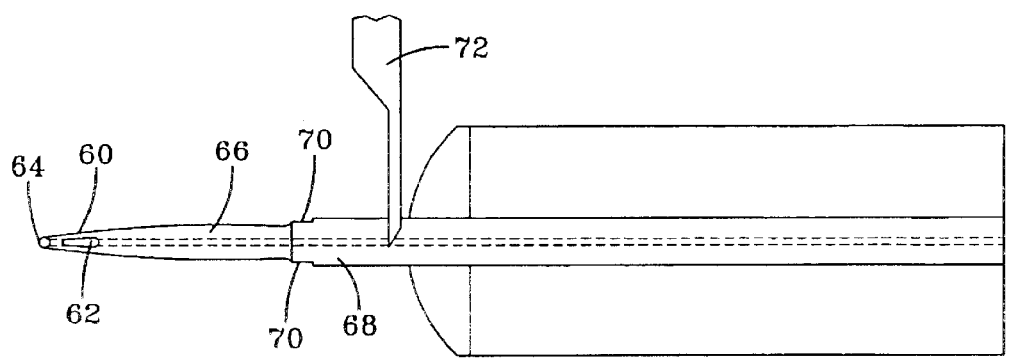
FIG. 8 is a view like FIG. 7 illustrating a still further step in the machining process of making tools in accordance with the invention.

The outer end of the stock is then turned with the cutting tool 56 to form a tapered section 60, which forms a tip 64 of the tool, as shown in FIG. 7. As the tapered tip of the shaft is formed, the bore runs out forming a port 62. The location of the bend as in FIG. 6 establishes the location of the port 62 from the point 64 of the workpiece. Thereafter, the turning of the dental tool is completed in the lathe so that the general shape and size of the dental tool is finished as illustrated in FIG. 8. An elongated shaft 66 is formed with a hub 68 having flats for engagement by a wrench. The hub is then formed with a bore that is threaded to mount on a transducer shaft. The tip is then bent at the appropriate point in front of the port as seen in FIG. 8. The tool is then severed from the end of the stock by a cutoff tool 72. Some or all of the bending may take place while in the lathe. Alternatively, all of the bending can be performed after the tool blank is removed from the lathe.

The tool blank is shaped to the desired final configuration by bending and forming the tip so that fluid flows from the port onto the tip at the desired position. A variety of other bends may be made in the shaft or shank to provide the desired final configuration. The tool may undergo other treatments including roughening and heat treating as discussed hereinafter.

These tools may be modified in any number of ways to provide the best structure and features for performing various procedures, including scaling, drilling, root canal and the like. Various heat and other treating and hardening processes may also be utilized in preparing the various tools for their ultimate intended purposes. Likewise, various coatings may be applied to the tip to achieve its purpose.

The tool is preferably constructed of a good medical grade of stainless steel or a titanium alloy of a medical grade. Medical grade alloy means a material that may be used in contact with food and with a patients body without undergoing a chemical reaction. A titanium alloy that the inventor has found preferable in the present application is identified as 6AL/4V ELI & CP Grade 4 and is available from President Titanium of Hanson, Mass. The inventor has found this material to be sufficiently hard, durable and flexible to resist breakage under use. It was also found to withstand heat for short durations of use in the absence of a cooling fluid without burning or melting. Tools can be made smaller with the titanium alloys than have ever been achieved before with the stainless steels. They can be made very small with very small tips that will withstand the rapid buildup of heat normally encountered in orthodontal applications. Other titanium alloys may also be used.

The above-described alloy has about 5.5 to about 6.5% aluminum, about 3.5 to about 4.5% vanadium, about 0.25% of iron, about 0.05% nitrogen, about 0.08% of carbon and about 0.015% of hydrogen. This material has an ultimate tensile strength of about 130,000 psi, and a use strength of about 120,000 psi. It has a Rock-well-C hardness of 30/34. While this material has been known for uses such as for surgical appliances and implants, orthopedic implants and the like, applicant has found no suggestion of its use in dental tools, as set forth herein.

Other titanium alloys and their properties and specifications which may be suitable for the herein use are available from the aforementioned supplier. For example 6AL/4V, CP Grade 2 and CP Grade 4. Specifications for machining, heat treating and other technical data and specifications for manufacture and use of various alloys of titanium is available from President Titanium in a Machining and Technical data handbook. In many applications, applicant has found that these materials can be used for the tools herein without the necessity for heat treating.

The applicant has found that the titanium material discussed herein is suitable for a long line of ultrasonic dental tools, as will be hereinafter described. Ultrasonic tools for dental work must be very small, durable and heat-resistant. Such tools must also be easily matched or tuned to an ultrasonic generator.

A modification may be made wherein the ultrasonic dental tip is provided with a roughened area extending from near curved radius portion to pointed end. The roughened area provides a coarse abrasive surface that will cut along any part of the roughened surface.

Preferably the roughing of the surface is performed by sand blasting the desired area with a microetcher or microblaster using approximately 400 grit powder. A suitable choice for such a sandblaster is provided by Danville Engineering Inc., of Danville Calif., and is available by the model name of "S-2 Precision Microsandblaster." It is preferable to operate the sandblaster by supplying pneumatic pressure of about 60–120 pounds-per-square inch, although it will be apparent to one skilled in the art that a suitable hydraulic pressure could be provided.

The roughening of the tool surface is preferably carried out after any hardening and before any coating process. The roughening is a less expensive process than coating with diamond particles. It also enables the construction and preparation of more precise and accurate tips.

Figure 9:
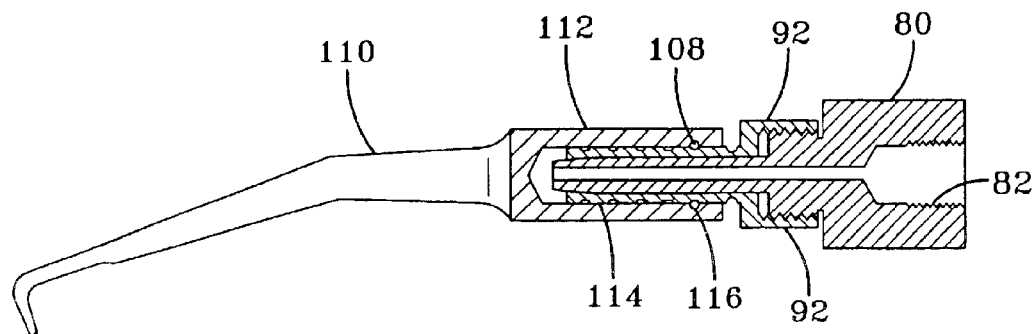
FIG. 9 is a view of the ultrasonic dental tool of the present invention having a quick disconnect adaptor assembly.
Figure 10:
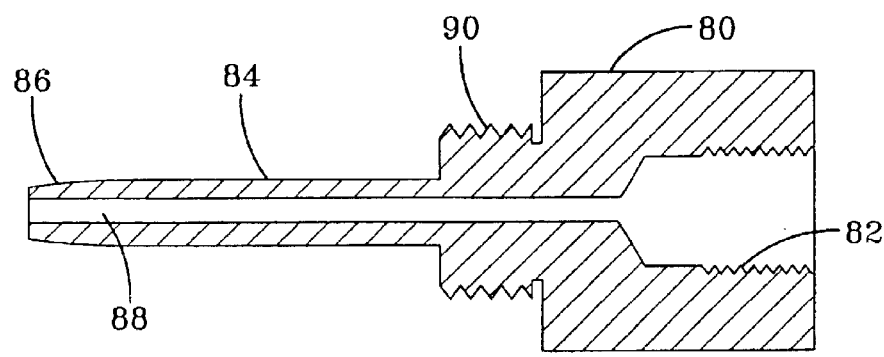
FIG. 10 is a cross-sectional view of the adaptor piece of the quick disconnect adaptor assembly.
Figure 11:
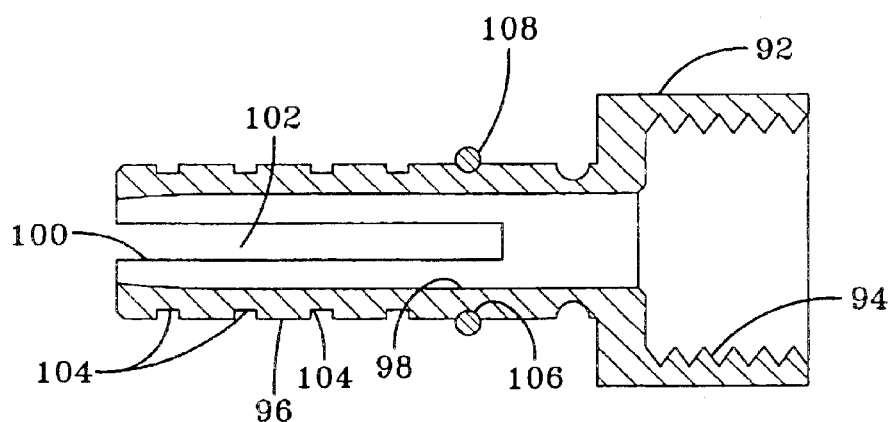
FIG. 11 is a cross sectional view of the connector sleeve of the quick disconnect adaptor assembly.

Referring to FIGS. 9 through 11, a quick connect adaptor for enabling the quick changing of the dental tools is illustrated. The quick change coupling assembly according to the invention comprises an adaptor piece 80 having a hub with a threaded socket 82 adapted to fit a hand piece of an ultrasonic generator. The adaptor 80 is provided with a forwardly axially extended elongated shaft 84 having a tapered tip or end 86 that function as a cam as will be described. A water passage 88 is formed in and extends from the coupling socket 82 through the tip 86 of the shaft to communicate with a passage in a tool. A threaded stud 90 is formed on the end of the connecting hub 80 at the juncture of the member 84 for cooperating with threads on a connector sleeve hereinafter described. The adapter piece 80 may be formed as an integral part of the hand piece of the ultrasonic generator.

A connector sleeve 92 as best illustrated in FIG. 11 has a hub formed with a threaded socket 94 at one end and an elongated split sleeve member 96 extending axially thereof. The sleeve 96 has an elongated internal generally cylindrical bore 98 with a generally conical shaped end portion 100 that acts as a cam. The wall of the sleeve is formed with a slot only one of which 102 is shown on opposite sides thereof. These slots enables the sleeve to expand as will be subsequently explained.

The outer surface of the sleeve is formed with a plurality of annular grooves 104 along the length thereof to aid in gripping the internal cylindrical wall of the mounting socket of the dental tool. An annular groove 106 is provided with an elastomeric o-ring 108 to position the ultrasonic tool as will be explained.

Referring now specifically to FIG. 9, an ultrasonic dental tool 110 has a hub 112 with a coaxial generally cylindrical mounting socket 114. An annular groove 116 is provided or formed in the inner cylindrical mounting socket bore of the tool to receive the elastromeric o-ring 108 when the socket is forced onto the sleeve 92. In operation the sleeve 92 mounted on the shaft 84 with threads 94 engaging threads 90 backed off from the threads 90 on the adaptor 80 until the forward conical or cam portion 100 thereof backs off from the forward conical shape cam 86 of the member 84. It will be apparent that only one of the cam surfaces 86 and 100 may be required. In other words either one of the cams may be present and the other absent. The hub of a tool is placed on the outer surface of the sleeve until the annular groove 116 snaps over the o-ring 108. Thereafter the sleeve 92 is rotated by hand threading the threads 94 onto the threaded portion 90 until the sleeve is cammed and expands into tight engagement with the internal bore 114 of the hub of the tool. This adapter assembly enables the quick detachable connection and removal of tools on a hand piece of an ultrasonic generator.

While I have illustrated and described my invention by means of specific embodiments, it is to be understood that numerous changes and modifications may be made therein without departing from the spirit and the scope of the invention as defined in the appended claims.

I claim:

1. A quick change connector for a dental tool, comprising:
   an ultrasonic dental tool;
   a generally cylindrical mounting socket on said tool;
   an elongate shaft on a hand piece of an ultrasonic generator;
   an expandable sleeve adapted for mounting on said shaft and extending into said socket; and
   a cam member on one of said sleeve and shaft operatively camming said sleeve into engagement with said mounting socket.

2. The quick change connector of claim 1, wherein said shaft and said sleeve have threads for moving said sleeve axially along said shaft to affect said camming.

3. The quick change connector of claim 2, wherein said shaft and said sleeve have each have a cam member thereon.

4. The quick change connector of claim 1, wherein:
   said sleeve has an annular circumferential member thereon; and
   said socket has a circumferential groove for engaging said circumferential member for positioning said socket.

5. The quick change connector of claim 1, wherein:
   said sleeve has at least one annular circumferential groove thereon adapted to enhance gripping of said socket by said sleeve.

6. A dental tool for use with an ultrasonic transducer, the tool comprising:
   a substantially elongate tool defined by a shaft having a proximal end with a quick connect connector at said proximal end for attachment to an ultrasonic transducer, and a distal end having a tip configured for performing a dental procedure, the proximal end including a hub having a generally cylindrical mounting socket; and
   a fluid passage extending from said proximal end to a port configured and positioned to direct fluid onto said tip;
   wherein said quick connect connector comprises an adaptor piece and a connector sleeve,
   the adaptor piece having a proximal end and a distal end, the proximal end having an attachment means adapted for attachment to a hand piece of an ultrasonic generator and the distal end being a shaft extending from the attachment means,
   the connector sleeve comprising an elongated split member adapted for mounting on said shaft and extending into said cylindrical mounting socket of said hub, and
   a cam member on one of said split member and said shaft camming said split member into engagement with said mounting socket.

7. The dental tool of claim 6, wherein said adaptor piece and said connector sleeve have threads for moving said sleeve axially along said shaft of said adaptor piece to affect said camming.

* * * * *